US010695025B2

(12) United States Patent
Gambhir et al.

(10) Patent No.: US 10,695,025 B2
(45) Date of Patent: Jun. 30, 2020

(54) WEARABLE ULTRASONIC DEVICE FOR CIRCULATING TUMOR CELL DETECTION

(71) Applicant: The Board of Trustees of the Leland Stanford Junior University, Palo Alto, CA (US)

(72) Inventors: Milan S. Gambhir, Portola Valley, CA (US); Adam De La Zerda, Palo Alto, CA (US); Bryan D. Knysh, Saratoga, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 795 days.

(21) Appl. No.: 14/531,718

(22) Filed: Nov. 3, 2014

(65) Prior Publication Data

US 2015/0126861 A1    May 7, 2015

Related U.S. Application Data

(60) Provisional application No. 61/901,277, filed on Nov. 7, 2013.

(51) Int. Cl.
*A61B 8/08* (2006.01)
*A61B 8/00* (2006.01)
*A61B 8/06* (2006.01)

(52) U.S. Cl.
CPC ............ *A61B 8/085* (2013.01); *A61B 8/4227* (2013.01); *A61B 8/4427* (2013.01); *A61B 8/481* (2013.01); *A61B 8/06* (2013.01); *A61B 8/488* (2013.01); *A61B 8/5223* (2013.01)

(58) Field of Classification Search
CPC ....... A61B 8/085; A61B 8/4227; A61B 8/481; A61B 8/06; A61B 8/488; A61B 8/5223
See application file for complete search history.

(56) References Cited

U.S. PATENT DOCUMENTS

| 5,833,613 | A | * | 11/1998 | Averkiou | ................. A61B 8/06 600/440 |
| 6,352,683 | B1 | * | 3/2002 | ten Cate | ................ A61K 41/00 424/450 |
| 6,530,887 | B1 | * | 3/2003 | Gilbert | ................ G01S 7/52025 600/459 |
| 2001/0039381 | A1 | * | 11/2001 | Burns | ...................... A61B 8/06 600/443 |
| 2002/0065467 | A1 | * | 5/2002 | Schutt | .................... A61B 5/055 600/454 |

(Continued)

*Primary Examiner* — Peter Luong
(74) *Attorney, Agent, or Firm* — Beyer Law Group LLP

(57) ABSTRACT

An apparatus for detecting circulating tumor cells is provided. A support system for mounting on a patient is provided. An imaging system is attached to the support system. The imaging system comprises a transmitter and receiver system for generating and transmitting signals into the patient and receiving signals from the patient and a controller. The controller comprises a processor and computer readable media. The computer readable media comprises computer readable code for transmitting signals into the patient, computer readable code for receiving signals from the patent, and computer readable code for providing in vivo circulating tumor cell imaging agent data from the received signals from the patient.

12 Claims, 8 Drawing Sheets

(56) References Cited

U.S. PATENT DOCUMENTS

| | | | |
|---|---|---|---|
| 2004/0162484 A1* | 8/2004 | Nemoto | A61B 5/055 600/420 |
| 2009/0093728 A1* | 4/2009 | Hyde | A61B 1/041 600/476 |
| 2010/0228234 A1* | 9/2010 | Hyde | A61F 2/82 604/891.1 |
| 2011/0082373 A1* | 4/2011 | Gurley | A61B 5/681 600/454 |

* cited by examiner

FIG.4A
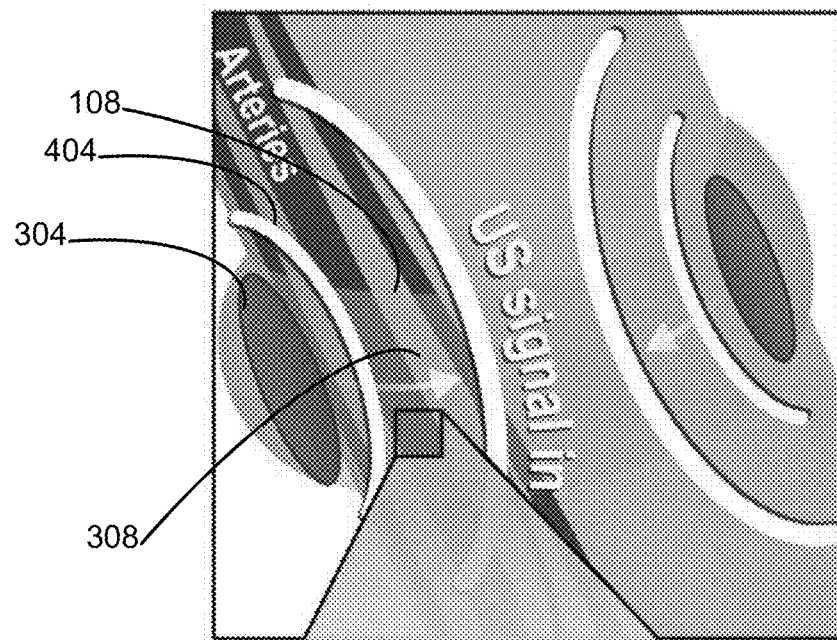
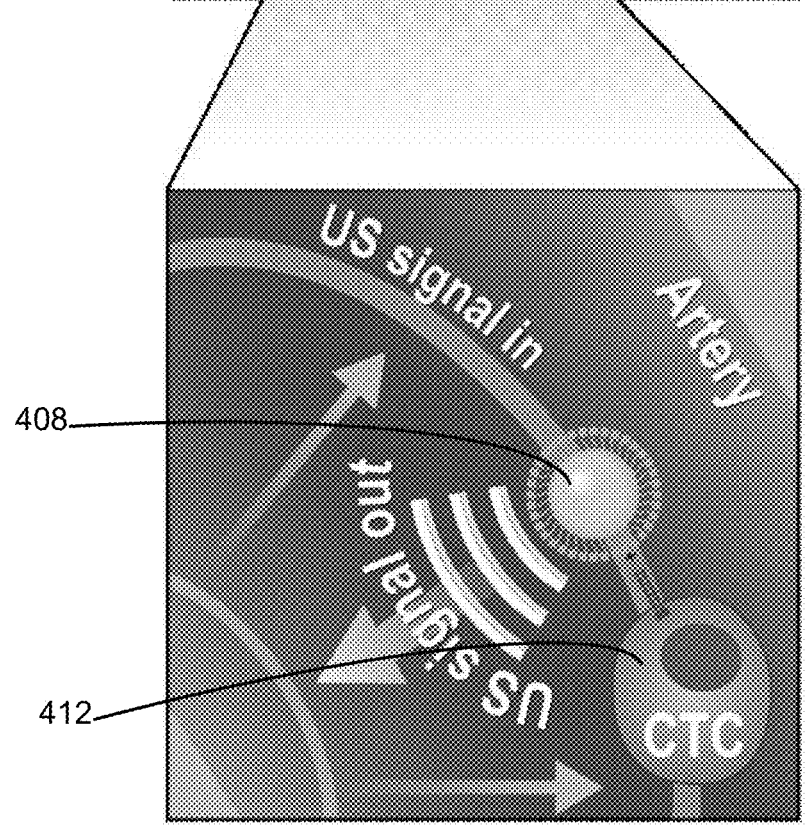
FIG.4B

- Analytical results from targeting experiment

WEARABLE ULTRASONIC DEVICE FOR CIRCULATING TUMOR CELL DETECTION

CROSS REFERENCE TO RELATED APPLICATIONS

This application claims priority under 35 U.S.C. § 119(e) from U.S. Provisional Application No. 61/901,277, entitled "WEARABLE ULTRASONIC DEVICE FOR CIRCULATING TUMOR CELL DETECTION", filed Nov. 7, 2013, by Gambhir et al.

GOVERNMENT RIGHTS

This invention was made with Government support under contract OD012179-01 awarded by the National Institutes of Health. The Government has certain rights in this invention.

BACKGROUND OF THE INVENTION

This invention relates generally to cancer detection devices. Metastasis is responsible for 90% of cancer-associated mortality. Relapses of cancers often occur when cancer cells originating from the primary tumor spread through the body via the circulatory system resulting in new tumor growth.

SUMMARY OF THE INVENTION

In accordance with the invention an apparatus for detecting circulating tumor cells is provided. A support system for mounting on a patient is provided. An imaging system is attached to the support system. The imaging system comprises a transmitter and receiver system for generating and transmitting signals into the patient and receiving signals from the patient and a controller. The controller comprises a processor and computer readable media. The computer readable media comprises computer readable code for transmitting signals into the patient, computer readable code for receiving signals from the patent, and computer readable code for providing in vivo circulating tumor cell imaging agent data from the received signals from the patient.

In another manifestation of the invention, a method for measuring trace cells is provided. An imaging agent for the trace cells is administered into a patient. The imaging agent is detected in the patient (in vivo). The detected imaging agent is used to measure a flow of trace cells flowing in blood vessels of the patient.

The invention and objects and features thereof will be more readily apparent from the following detailed description and appended claims when taken with the drawings.

BRIEF DESCRIPTION OF THE DRAWINGS

FIG. 4A is an enlarged view of the imaging agent detector.

FIG. 4B is an enlarged view of an artery of FIG. 4A.

DETAILED DESCRIPTION OF ILLUSTRATED EMBODIMENTS

Figure 1:
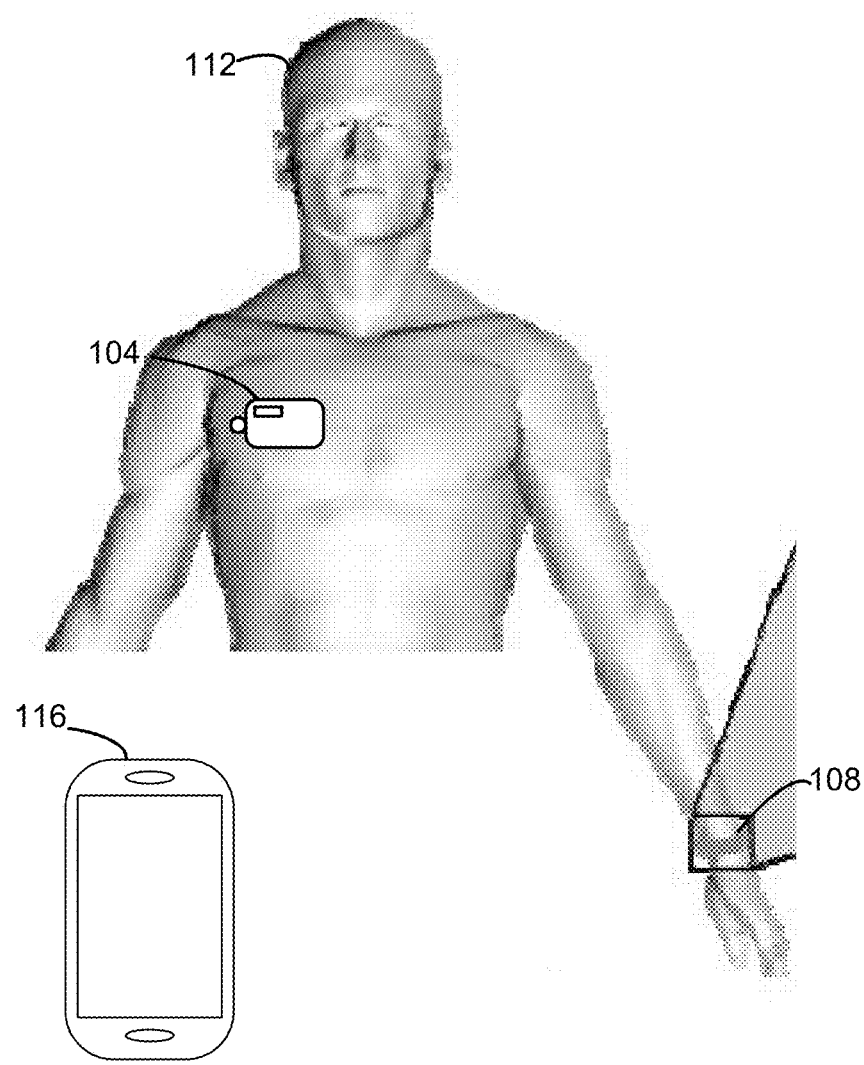
FIG. 1 is a schematic view of a system that is used to implement an embodiment of the invention.

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

Metastasis is responsible for 90% of cancer-associated mortality. Relapses of cancers often occur when cancer cells originating from the primary tumor spread through the body via the circulatory system resulting in new tumor growth. These circulating tumor cells (CTCs) can be identified by specific cell receptors, such as epithelial cell adhesion molecules (EpCAM receptors), on their surfaces.

Cancer occurs when cells divide and grow extremely rapidly in an unregulated manner. Cancer can spread to all parts of the body through the bloodstream or lymphatic system, a process known as metastasis. When a metastasis happens, cells from the primary tumor break off, spread to a new location, and begin to a form a new tumor. Unfortunately, metastasis is one of the main reasons why the survival rate for cancer patients is low. As cancer spreads through the body, it gets harder to treat. Even when treatment of the primary tumor is considered successful, there is still a chance of recurrence. According to a recent study in the Journal of the National Cancer Institute, 1 in 5 breast cancer survivors suffer a recurrence within just 10 years after treatment. Recurrence or relapse happens when initial treatment fails to kill off all the cancer cells or when a new tumor forms.

Researchers at Harvard found that as a tumor regrows, tumor cells begin to spread around the body via blood vessels. These circulating tumor cells (CTCs) can then plant themselves in an organ and begin to grow into a secondary tumor, or they can return to their initial start point and begin to regrow there. Unfortunately, not enough is known about CTCs to fully understand how they function and become tumors. However, CTCs are known to have epithelial cell adhesion molecules (EpCAM receptors) on their surfaces, which can easily be targeted with antibodies.

There is currently only one FDA-approved technique for detecting CTCs. CellSearch uses a 7.5 mL blood draw sample along with ferrofluid nanoparticles with antibodies that target EpCAM to magnetically separate CTCs from bulk blood cells, followed by a series of staining and image analysis by a highly trained clinician to identify specific CTCs. Studies show that the test can be highly inaccurate due to human errors in reading the images and sampling errors in the small blood draw. Another more accurate technique has been created that utilizes microfluidics to detect CTCs. However, any method that requires blood draws is less accurate due to small blood samples used, as compared to the 5 to 6 liters of blood in the human body. Other methods of recurrence detection include using magnetic resonance imaging (MRI), computed tomography (CT), and positron emission tomography (PET) to detect tumors. However, these imaging methods are expensive, require significant infrastructure, and lack the optimal spatial resolution for detection of cancer in its earliest stages. In addition, contrast agents used in PET scans are radioactive, expensive, and potentially harmful to patients if used frequently. Furthermore, contrast agents used for MRI and CT scans can cause harm such as renal damage.

Embodiments of the invention provide a CTC imaging agent that is able to attach to CTCs within the blood stream and a detector for detecting the CTC imaging agent in the blood stream.

Figure 2:
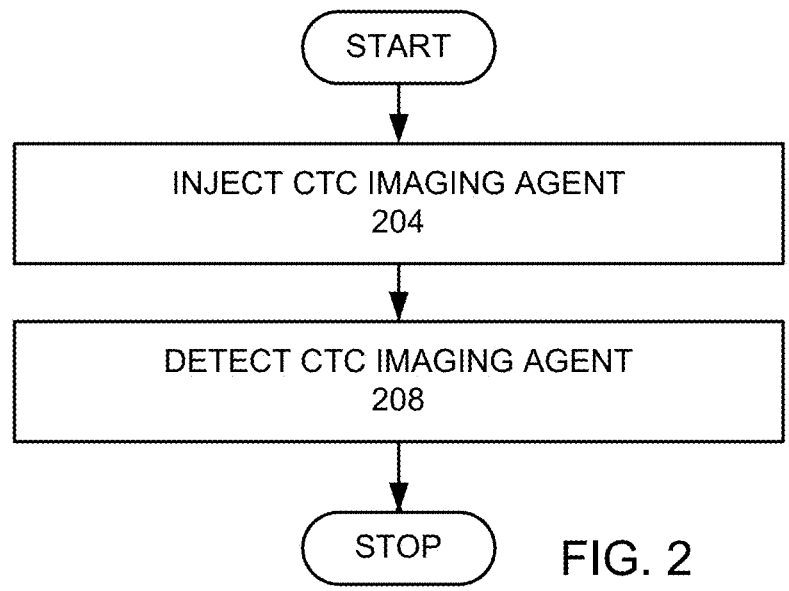
FIG. 2 is a flow chart of a process used in an embodiment of the invention.

FIG. 1 is a schematic view of a system that is used to implement an embodiment of the invention. In this embodiment, a CTC imaging agent injector 104 and an imaging agent detector 108 are connected to a body 112. A processing device 116 is located near the body 112. FIG. 2 is a flow chart of a process used in an embodiment of the invention. In an embodiment of the invention, the CTC imaging agent injector 104 injects an imaging agent into the body 112 (step 204). The imaging agent injector 104 may inject the microbubbles. The imaging agents attached to CTCs are detected by the imaging agent detector 108 (step 208). In this embodiment, the imaging agent detector 108 sends data to the processing device 116. The processing device 116 processes the data and sends a message to a remote device, which may be located at a hospital or doctor's office. In this embodiment, the processing device 116 is a smart phone, which communicates with the imaging agent detector 108 by Bluetooth or over Wi-Fi and which communicates with the remote device using a cellular telephone connection or the Internet.

Figure 3:
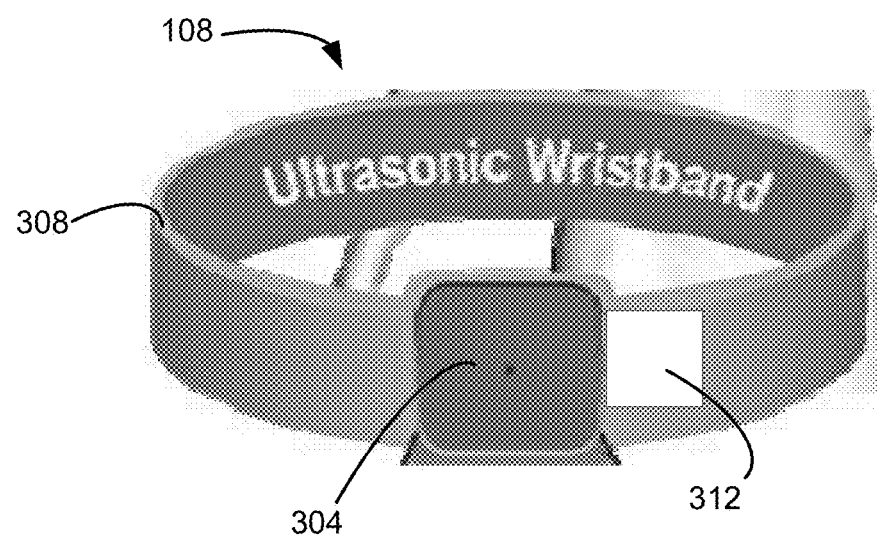
FIG. 3 is a more detailed view of the detector.

In an embodiment, the imaging agent is composed of microbubbles attached with antibodies targeted against CTCs. The detector is an ultrasonic transmitter and receiver, which detects the microbubbles flowing in the blood stream. FIG. 3 is a more detailed view of the detector 108. The detector 108 comprises of a wristband 308, an ultrasonic transmitter/receiver 304, and a controller 312. The wristband 308 allows attachment of the detector 108 to a wrist. The ultrasonic transmitter/receiver 304 transmits ultrasound waves into the body and detects a received signal. The controller 312 controls the ultrasonic transmitter/receiver 304, and may perform other functions, such as transmitting data to the processing device 116. FIG. 4A is an enlarged view of the imaging agent detector 108 on a wrist of FIG. 1. The ultrasonic transmitter/receiver 304 sends ultrasonic signals 404 into the wrist. FIG. 4B is an enlarged view of an artery of FIG. 4A. A microbubble 408 attached to a CTC 412. The microbubble 408 reflects higher frequency ultrasonic signals, making detection of such microbubbles easier to detect in ultrasound contrast mode.

Figure 5:
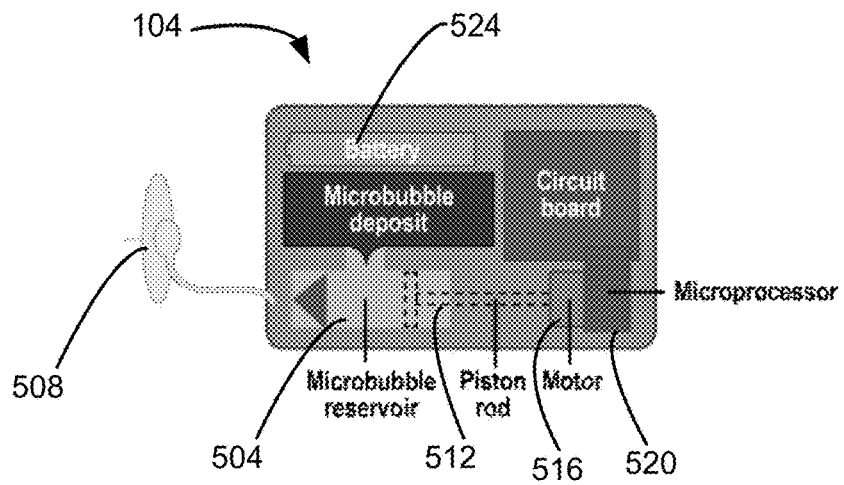
FIG. 5 is a more detailed schematic view of the imaging agent injector.

FIG. 5 is a more detailed schematic view of the imaging agent injector 104. The imaging agent injector 104 comprises a microbubble reservoir 504, an injector 508 in fluid connection with the microbubble reservoir 504, a piston 512 at a first end of the microbubble reservoir 504, a motor 516 connected to the piston 512, a controller 520 controllably connected to the motor 516 and a battery 524 for providing power to the controller 520 and the motor 516. In the alternative, separate batteries or other power sources may be used to provide separate power to the controller 520 and the motor 516. The controller 520 may have a communications device, a circuit board, and/or a microprocessor. The controller 520 causes the motor 516 to drive the piston 512, causing microbubbles in the microbubble reservoir 504 to be injected through the injector 508 into the subject.

Figure 6:
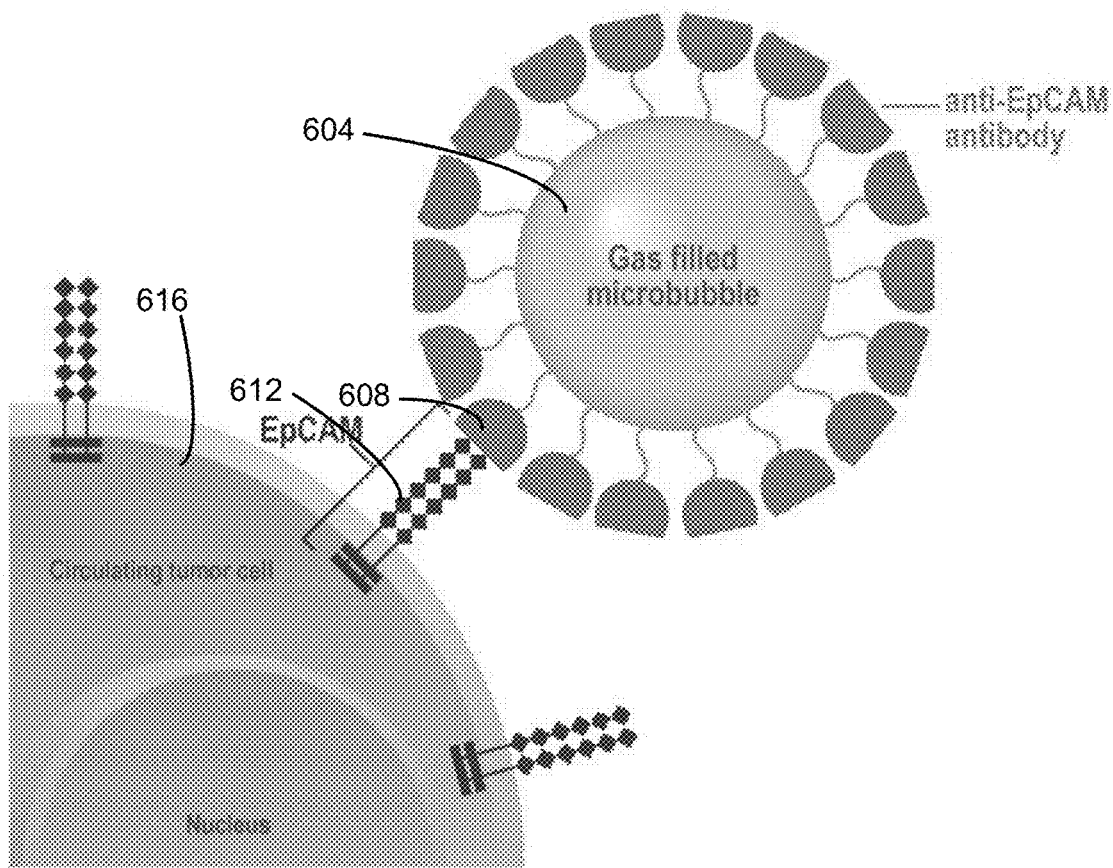
FIG. 6 shows a microbubble with a coating of anti-EpCAM antibodies

In an embodiment of the invention, microbubbles were filled with perfluorobutane and their surfaces composed of phospholipids. In addition, the microbubbles are approximately 1-5 microns in diameter and covered in a protein called streptavidin. Streptavidin creates a high affinity bond with another protein called biotin, so biotinylated antibodies are most effective with these microbubbles. Microbubbles (MBs) are used as an ultrasound contrast agent because of their unique ultrasound properties. When ultrasound waves come into contact with MBs, the MBs return ultrasound waves of the same and varying frequencies. Therefore, by coating microbubbles with anti-EpCAM antibodies, these MBs would easily be able to latch onto circulating tumor cells and be imaged using an ultrasound device. FIG. 6 shows a microbubble 604 with a coating of anti-EpCAM-antibodies 608. The anti-EpCAM-antibodies 608 bind to receptors 612 of a CTC 616.

Figure 12:
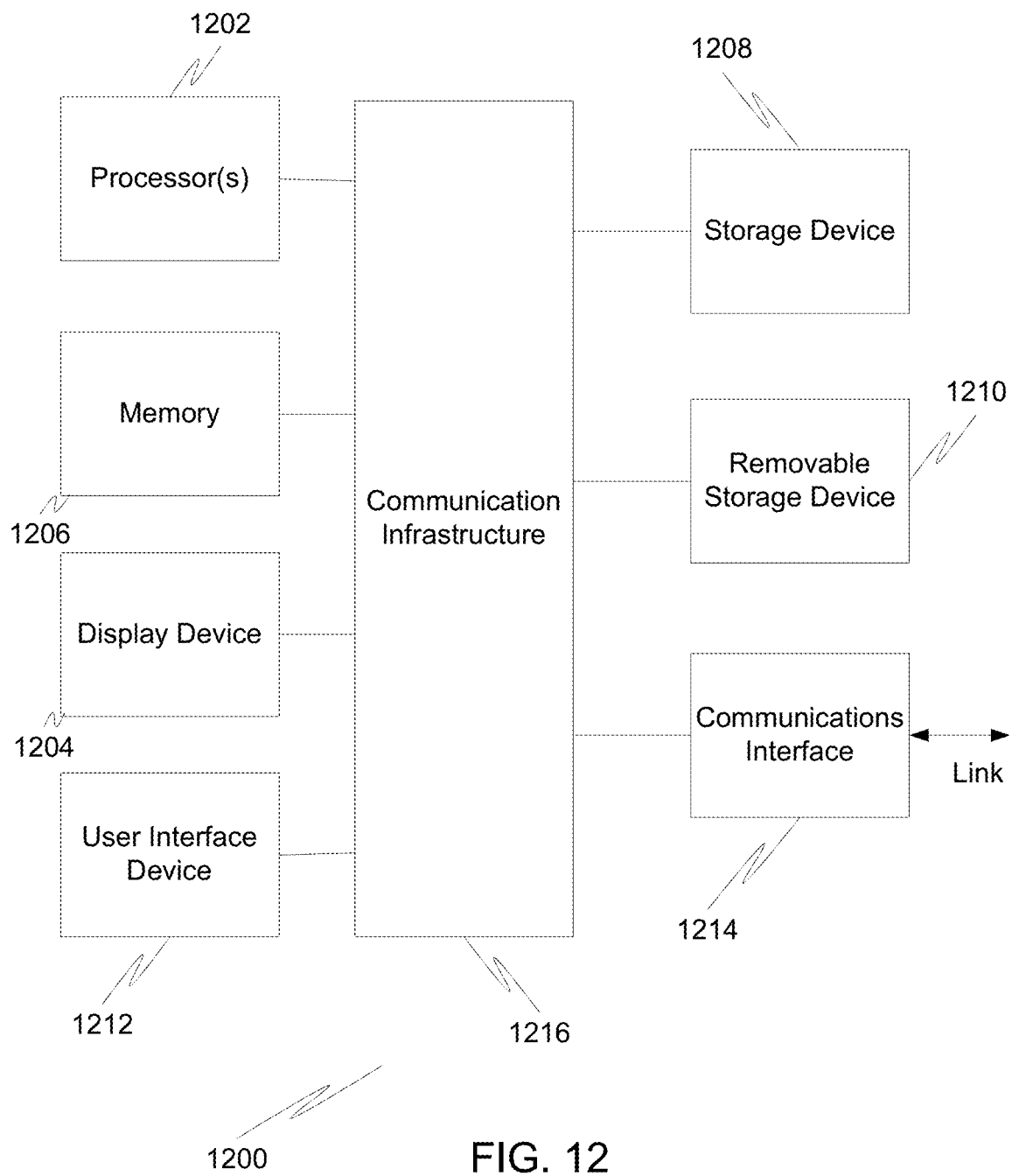
FIG. 12 is a schematic view of a computing system that may be used in an embodiment of the invention.

FIG. 12 is a high level block diagram showing a computer system 1200, which is suitable for implementing the controller 312 or the processing device 116 used in embodiments of the present invention. The computer system may have many physical forms ranging from an integrated circuit, a printed circuit board, and a small handheld device up to a huge super computer. The computer system 1200 includes one or more processors 1202, and further can include an electronic display device 1204 (for displaying graphics, text, and other data), a main memory 1206 (e.g., random access memory (RAM)), storage device 1208 (e.g., hard disk drive), removable storage device 1210 (e.g., optical disk drive), user interface devices 1212 (e.g., keyboards, touch screens, keypads, mice or other pointing devices, etc.), and a communication interface 1214 (e.g., wireless network interface). The communication interface 1214 allows software and data to be transferred between the computer system 1200 and external devices via a link. The system may also include a communications infrastructure 1216 (e.g., a communications bus, cross-over bar, or network) to which the aforementioned devices/modules are connected.

Information transferred via communications interface 1214 may be in the form of signals such as electronic, electromagnetic, optical, or other signals capable of being received by communications interface 1214, via a communication link that carries signals and may be implemented using wire or cable, fiber optics, a phone line, a cellular phone link, a radio frequency link, and/or other communication channels. With such a communications interface, it is contemplated that the one or more processors 1202 might receive information from a network, or might output information to the network in the course of performing the above-described method steps. Furthermore, method embodiments of the present invention may execute solely upon the processors or may execute over a network such as the Internet in conjunction with remote processors that shares a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

In order to achieve early detection of cancer recurrence at a low cost, an embodiment of the invention uses a wearable ultrasonic device for autonomous cancer detection, which would be worn by cancer patients after initial treatment. The device would function using an ultrasound band over a blood vessel, a loading compartment connected to the patient's chemo port, and an effective targeted contrast agent.

In this embodiment, the microbubbles (MBs) coated with anti-EpCAM antibodies are injected into the patient. Time is provided for the targeted MBs to latch onto any CTCs. After waiting for a set amount of time, the ultrasound portion of the device would become active. The ultrasound wristband would emit continuous ultrasound signal into the blood vessels below and process the returning signal. MBs give back a strong and unique signal, which the device would recognize, and then alert the user/user's doctor when an MB/several MBs bound to a circulating tumor cell crosses by. The device would only recognize MBs targeted to circulating tumor cells because enough time will be given after injection to ensure that the MBs not bound to CTCs would be flushed out of the patient. This embodiment would be able to autonomously detect cancer recurrence at its earliest stages, before conventional detection methods would be able to. This would allow doctors to treat a wide range of patients earlier and more effectively, and increase cancer patient survival rates across the board.

EXPERIMENTS

Due to the difficulty and impracticality of growing circulating tumor cells in culture, experiments were performed on U87 human primary glioblastoma cells that express $\alpha v \beta 3$-integrin. Circulating tumor cells are hard to retrieve and there are currently no circulating tumor cell lines. Therefore, due to similar binding properties of antibodies to $\alpha v \beta 3$-integrin and EpCAM, we concluded that performing experiments on U87 cells would be a suitable proxy to prove the concept for our device. Cells were grown with MEM Alpha Modification 1× and split once a week to maintain the confluency of the cells. Microbubbles targeted for $\alpha_v \beta_3$-integrin ($MB_{\alpha v \beta 3}$) were created by conjugating biotinylated anti-$\alpha_v \beta_3$ antibodies to perfluorobutane-filled microbubbles with streptavidin on their surface. For the flow chamber experiment, which was performed to test the targeting of $MB_{\alpha v \beta 3}$ to U87 cells in similar conditions as a blood vessel, mouse IgG1 K isotype control antibodies attached to streptavidin-coated microbubbles ($MB_{isotype}$) and a blocking study using purified anti-$\alpha_v \beta_3$ antibodies were the two controls tested. For the first few experiments, the microbubble samples were conjugated with biotinylated fluorescein isothiocyanate (FITC) in order to view samples of U87 cells and microbubbles under a fluorescent microscope. The attachment of the different microbubbles to the U87 cells was tested by running them through a flow chamber containing the cells, and fluorescent images were then acquired. In the last experiment, $MB_{\alpha v \beta 3}$ bound to U87 cells and two control samples ($MB_{\alpha v \beta 3}$ alone and U87 cells alone) were run through an agarose phantom and the ultrasound signal measured using a 25 MHz VisualSonics transducer connected to a VisualSonics Vevo2100 Ultrasound System.

The target-ready microbubbles (MBs; VisualSonics Inc., Toronto, Ontario, Canada) were composed of perfluorobutane/nitrogen gas ($C_4F_{10}/N_2$) and a phospholipid shell covered with streptavidin molecules, and arrived at a stock concentration of $1.6 \times 10^9$ MBs/vial. All the MBs synthesized in the experiments ($MB_{FITC}$, $MB_{PBS}$, $MB_{isotype}$, and $MB_{\alpha v \beta 3}$) were first reconstituted by adding 1 mL of phosphate buffered saline 1× (PBS 1×) to individual vials of microbubbles. Microbubbles bound only to biotinylated FITC ($MB_{FITC}$) were created by conjugating 100 µL of constituted MBs (at stock concentration) with 75 ng of biotinylated FITC molecules (15 µL of biotinylated FITC at 5 µg/mL from Biotium, Inc) to fully saturate the MBs with FITC. Using tape, tubes of $MB_{FITC}$ were then attached to a rocker (Fisher Scientific Nutating Mixer) and allowed to mix for 3 hours to ensure that all the biotinylated FITC molecules bound to the MBs and that no streptavidin molecules on the surface of the MBs were left unbound. Microbubbles mixed with additional PBS ($MB_{PBS}$) were created by mixing 100 µL of constituted MBs (at stock concentration) with 15 µL of additional PBS and then placing the mixture on the same rocker for 3 hours. Microbubbles ($MB_{\alpha v \beta 3}$) targeted against Alpha V Beta 3 Integrin ($\alpha v \beta 3$, present on U87 cells) were synthesized by combining 100 µL of constituted MBs (at stock concentration), 6 µg of biotinylated human anti-$\alpha v \beta 3$ antibodies (12 µL of antibodies at 0.5 mg/mL from Ebioscience) and 75 ng of biotinylated FITC molecules (15 µL of FITC at 5 µg/mL). After adding the biotinylated human anti-$\alpha v \beta 3$ antibodies and biotinylated FITC molecules to the MBs, we gently agitated the mixture by hand and then let it incubate on ice for 15 minutes. Isotype control microbubbles ($MB_{isotype}$) were synthesized in a similar way as the $MB_{\alpha v \beta 3}$, but biotinylated mouse IgG1 K isotype control antibodies were used instead of the biotinylated human anti-$\alpha v \beta 3$ antibodies.

U87 cells (human primary glioblastoma from a 44 year old patient) were grown in a 225 cm$^2$ cell flask (BD Falcon Cell Culture Flask) with MEM Alpha Modification 1× cell media and split once a week using trypsin. Media was changed once every 2-3 days to maintain the condition of the cells.

In a first experiment, $MB_{FITC}$ were used in order to view the microbubbles under a fluorescent microscope, and to easily distinguish microbubbles from U87 cancer cells. As a control, $MB_{PBS}$ were created and tested as well. 15 µL of $MB_{FITC}$ and $MB_{PBS}$ each were put on a glass slide (Thermo Scientific UltraStick Glass Slide). We put the $MB_{FITC}$ on the left side of the slide and the $MB_{PBS}$ on the right side on the slide. After the samples were put on the slide, both sides of the slide were covered with a transparent slip, and nail polish was added on all sides to ensure the slips would not fall out. Then, the slide was imaged using a fluorescent microscope (Zeiss LSM 510 NLO 2-photon confocal microscope) at 10×, 20×, and 63× magnification using both fluorescence and bright field settings. After successful visualization of $MB_{FITC}$ was performed, further fluorescence imaging was performed to view $MB_{FITC}$ with U87 cancer cells. U87 cells were grown in 4 spots on an 8-well plate (BD Falcon 8-well Cell Culture Slide), with each well containing 200 µL of MEM Alpha 1× Media and $10^4$ U87 cells (10 µL of cells at a concentration of $10^3$ cells/µL). 15 µL of $MB_{FITC}$ was added to 2 of the wells, 15 µL of $MB_{PBS}$ was added to one of the wells, and nothing was added to the last well. The 8-well plate was then modified into a slide, and transparent slips were added and secured with nail polish. The slide was then imaged with the same fluorescent microscope at 10×, 20×, and 63× magnification using both fluorescence and bright field settings.

In a second experiment, targeted MBs were created and their effectiveness tested. First, a glass slide (Ibidi μ-Slide VI$^{0.4}$) was coated with 75 μg/ml of fibronectin and seeded with 3×10$^5$ U87 cells, which were allowed to grow overnight at 5% $CO_2$. Then, to create the flow chamber, the prepared slide was attached to a syringe pump (Kent Scientific GenieTouch Syringe Pump) using a flow kit (Ibidi μ-Slide VI Flow Kit). The flow chamber was then inverted and set underneath a fluorescent microscope (Zeiss Axio Vert 200M Fluorescence Microscope), with one end leading to the syringe pump and the other end leading into a waste container. To test the attachment of $MB_{\alpha v \beta 3}$ to the U87 cells on the slide, the $MB_{\alpha v \beta 3}$ were run through the flow chamber. Microbubbles flowed over the cells at a rate of 0.1 ml/min, which is equivalent to 5.0×10$^6$ MBs flowing over the cells/min. $MB_{\alpha v \beta 3}$ ran through the flow chamber for 4 minutes, which translates to 2.0×10$^7$ MBs flowing over the cells in total. While the syringe pump was pushing the $MB_{\alpha v \beta 3}$ over the cells, we recorded videos to examine the attachment mechanism of the $MB_{\alpha v \beta 3}$. After the syringe pump had pushed the $MB_{\alpha v \beta 3}$ over the cells, we captured images using fluorescence and brightfield settings at 20× and 40× magnification. The two controls performed were $MB_{isotype}$ and a blocking study. $MB_{isotype}$ were run through the flow chamber and pushed over U87 cells to further prove the successful binding between the biotinylated human anti-αvβ3 antibodies and the αvβ3 receptors on the U87 cells. The blocking study was performed by first running blocking antibodies (purified anti-human CD51/CD61 from Ebioscience) through the flow chamber. Then, $MB_{\alpha v \beta 3}$ were run through the flow chamber. Both controls were run through the flow chamber and imaged using the fluorescent microscope in a similar manner as the primary test.

In a third experiment, the agarose phantom was created by first mixing 0.5 g of standard, low, electroendosmosis agarose (from J. T. Baker) with 49.5 mL of distilled water (Millipore Water) in a 50 mL flask. The flask was then put in a microwave (Daewoo 1.1 Cu. Ft. White Countertop Microwave) and heated for 40 seconds until the mixture boiled. The mixture was then added to a small, plastic, hexagonal weigh boat. After giving 2 minutes to let the agarose and water mixture cool down, a 2 mm inner-diameter piece of FEP plastic tubing (from McMaster-Carr) was held in the mixture in the shape of an arch until the agarose gel cooled completely and formed a gel with the tubing inside. In order to keep the agarose gel from drying, a few drops of tap water were added on top of the gel and saran wrap was applied on top of the phantom First, $MB_{\alpha v \beta 3}$ bound to U87 cells were synthesized. 16.3 μL of $MB_{\alpha v \beta 3}$ (at stock concentration), 5×10$^5$ U87 cells (727 μL of U87 cells at 6.88×10$^5$ U87 cells/mL), and 257 μL of MEM Alpha Modification 1× cell media were placed into an Eppendorf tube. The tube was then put on a scientific rotisserie for 1 hour, allowing the sample to mix thoroughly. After, the sample was allowed to incubate on ice and 500 μL were removed from the top using a vacuum. Two controls, U87 cells alone and $MB_{\alpha v \beta 3}$ alone were created in a similar manner. For the first control ($MB_{\alpha v \beta 3}$ alone), 16.3 μL of $MB_{\alpha v \beta 3}$ (at stock concentration) and 984 μL of MEM Alpha Modification 1× cell media were placed into an Eppendorf tube. For the second control (U87 cells alone), 5×10$^5$ U87 cells (727 μL of U87 cells at 6.88×10$^5$ U87 cells/mL) and 273 μL of MEM Alpha Modification 1× cell media were placed into an Eppendorf tube. Both controls were subject to the same mixing and removal process as the $MB_{\alpha v \beta 3}$ bound to U87 cells. During imaging, the samples were removed from their respective Eppendorf tubes using a 20-gauge needle (BD 20 G×1 in. Precision Guide Needle) connected to a 5 mL syringe (FisherScientific Sterile 5 mL NORM-JECT, Luer Lock syringe) to avoid any potential damage to the samples caused by using a higher gauge needle. Each time a sample was fully loaded into a syringe, we removed the needle so the syringe could connect to the syringe pump. Next, the syringes with the different samples were loaded separately onto a syringe pump (SmithsMedical Graseby 3400 Syringe Pump). The syringes were then connected individually to one end of a 1 mm inner-diameter plastic, small bore extension (Smiths Medical 61 in. Small Bore Extension with Non-Removable Blue Slide Clamp, Male). The small bore extension was cut about 4 in. from where the syringe was connected and was then inserted into the FEP plastic tubing in the agarose phantom using super glue (Gorilla Super Glue). Then, 8 inches from the other end of the small bore extension was cut off and attached to the other side of the FEP plastic tubing using super glue. This end of the small bore extension lead to a waste container. The syringe pump was turned on and ran at 15 mL/hr while the phantom (placed on a Vevo Rat Handling Table) was imaged using a 25 MHz probe attached to a VisualSonics Vevo2100 Ultrasound System. Along with acquiring images in the standard B-mode, contrast mode images were taken as well. Contrast mode is specifically designed to detect the presence of microbubbles by looking at differences between the echogenicity of the samples and of the microbubbles. Once we finished imaging each sample, we loaded 2.5 mL of PBS into the syringe pump and allowed it to wash out any remaining fluid through the tube and into the waste container.

All image analysis was performed using Image J 1.46r on a 10.9.3 MacBook Air. In the experiments, p values of less than 0.05 were considered statistically significant. Using a one-sided Student's T-test, we analyzed the statistical significance of the difference in attachment to U87 cells of the tests in the flow chamber studies. Statistical analysis was performed in order to determine whether the attachment of $MB_{\alpha v \beta 3}$ to U87 cells was statistically different than the attachment of the controls to U87 cells.

Results

In the flow chamber experiment, $MB_{\alpha v \beta 3}$ had a much higher attachment rate to U87 cells in the flow chamber than $MB_{isotype}$ and the blocking study. In addition, the agarose phantom experiment shows that ultrasound signal from the $MB_{\alpha v \beta 3}$+U87 cells and $MB_{\alpha v \beta 3}$ alone in the phantom was significantly higher than the ultrasound signal from U87 cells alone.

Figure 7:
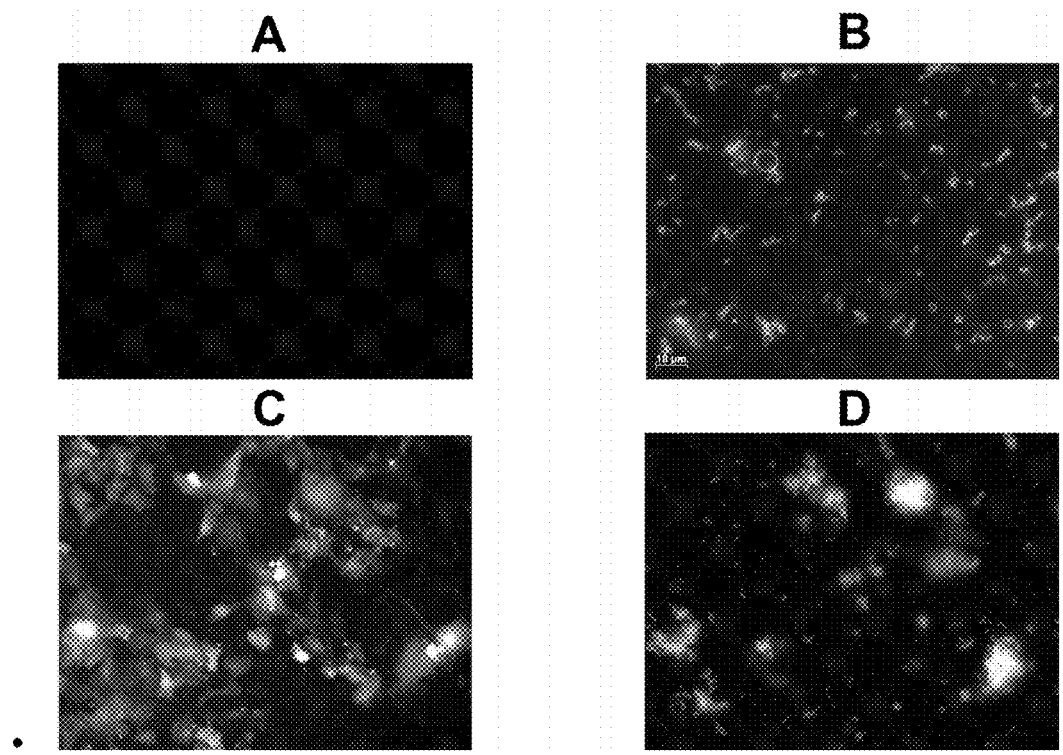
FIGS. 7A-D are images from a first experiment.
Figure 8:
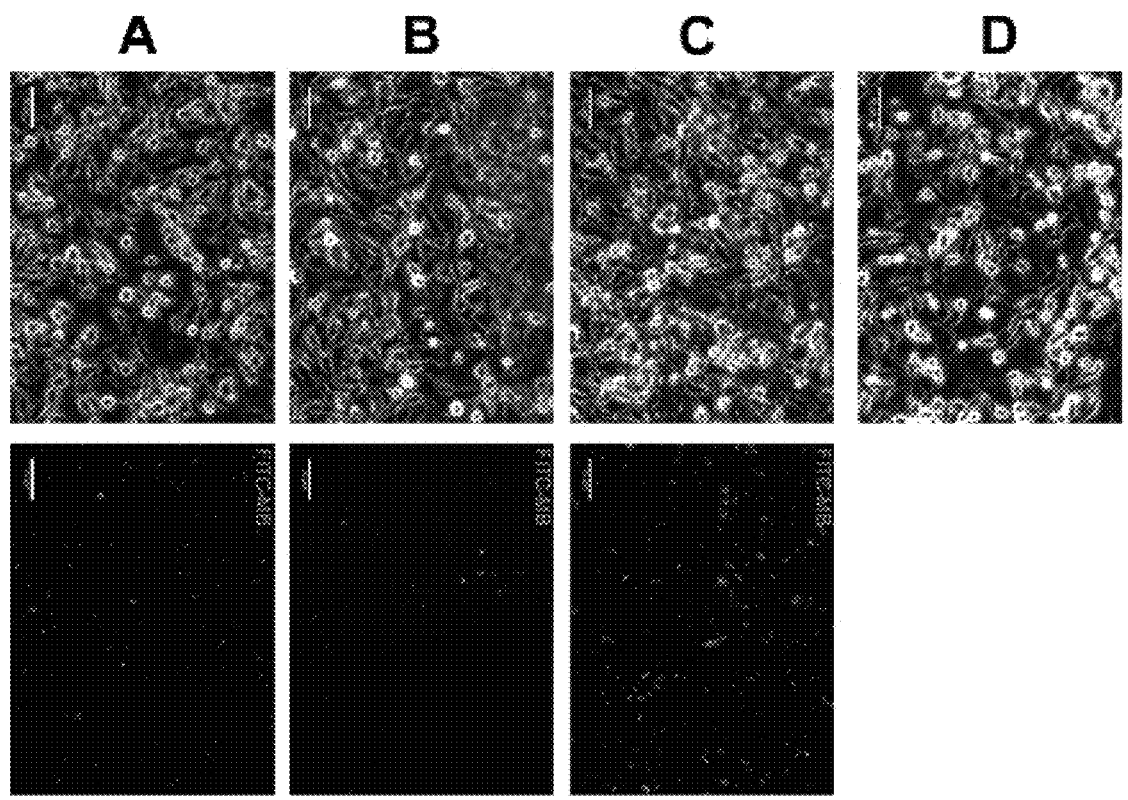
FIGS. 8A-D are images from a second experiment.

FIGS. 7A-D show $MB_{PBS}$ imaged using fluorescence settings in 7A, $MB_{FITC}$ imaged using fluorescence settings in 7B, U87 cells and $MB_{FITC}$ imaged using brightfield settings in 7C, and U87 cells with $MB_{FITC}$ imaged using fluorescence settings in 7D. After post-experiment image analysis, we determined that the fluorescent signal from $MB_{FITC}$ (FIG. 7B) was much higher than the signal from $MB_{PBS}$ (FIG. 7A). At the same contrast ranges, the signal from $MB_{PBS}$ was close to 0, compared to a higher signal from the $MB_{FITC}$. When the combination of U87 cells and $MB_{FITC}$ was observed under a fluorescent microscope (FIGS. 7C-D), it was found that the bright field settings could easily see the cells (FIG. 7C), but not the MBs, while the fluorescent settings could easily see the MBs (FIG. 7D), but not the cells. This experiment proved that using biotinylated FITC molecules would be an effective way of distinguishing MBs from cells, and that U87 cells naturally have a small fluorescence signal.

Figure 10:
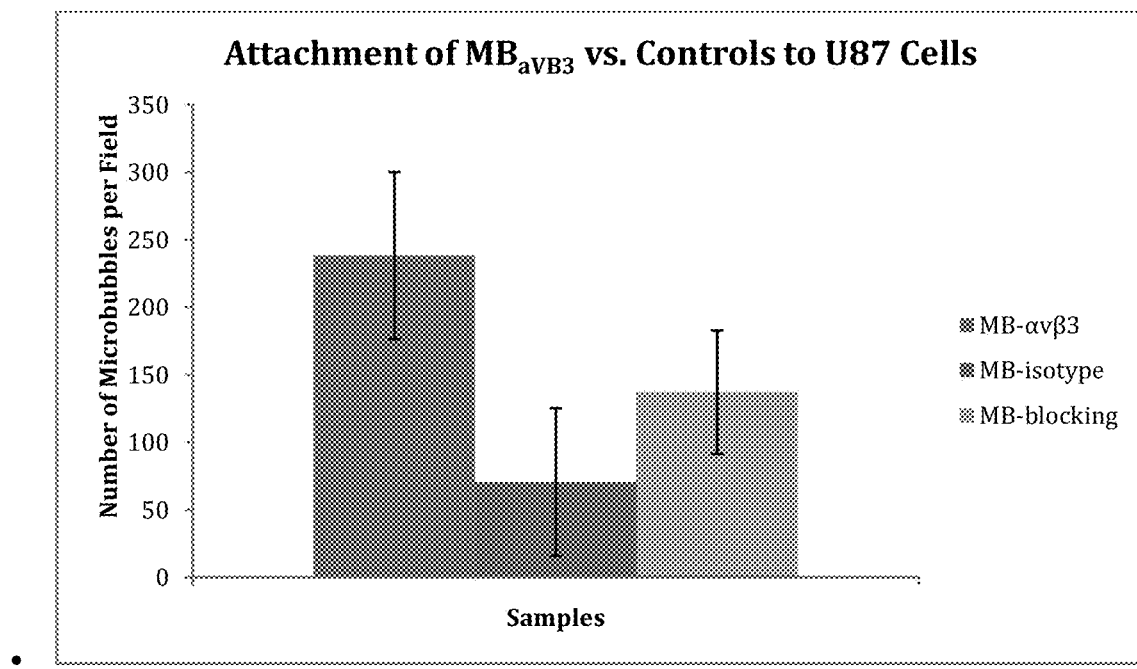
FIG. 10 is a graphical interpretation of the results from the second experiment.

FIGS. 8A-D shows the results from the flow chamber experiment; fluorescence (bottom image) and brightfield (top image) image of the blocking study in 8A, fluorescence and brightfield image of $MB_{isotype}$ in 8B, fluorescence and brightfield image of $MB_{\alpha v \beta 3}$ in 8C, and a brightfield image of U87 cells alone in 8D. Several images at 20× magnification from all three tests ($MB_{\alpha v \beta 3}$, $MB_{isotype}$, and the blocking study), and from just U87 cell alone, were analyzed using Image J to determine the number of microbubbles present per field. The U87 cells alone (FIG. 8D) had an average of 0 MBs/field, $MB_{\alpha v \beta 3}$ (FIG. 8C) had an average of 238.29±61.892 MBs/field, $MB_{isotype}$ (FIG. 8B) had an average of 70.50±54.775 MBs/field, and the blocking study (FIG. 8A) had an average of 137±45.758 MBs/field. These statistically significant ($p<1.6\times10^{-4}$, between $MB_{\alpha v \beta 3}$ and $MB_{Isotype}$) results show that $MB_{\alpha v \beta 3}$ had a higher attachment to U87 cells then the controls, as proof of concept for the attachment of targeted microbubbles to circulating tumor cells. Graphical interpretation of the results is displayed below under the graph of FIG. 10.

Figure 9:
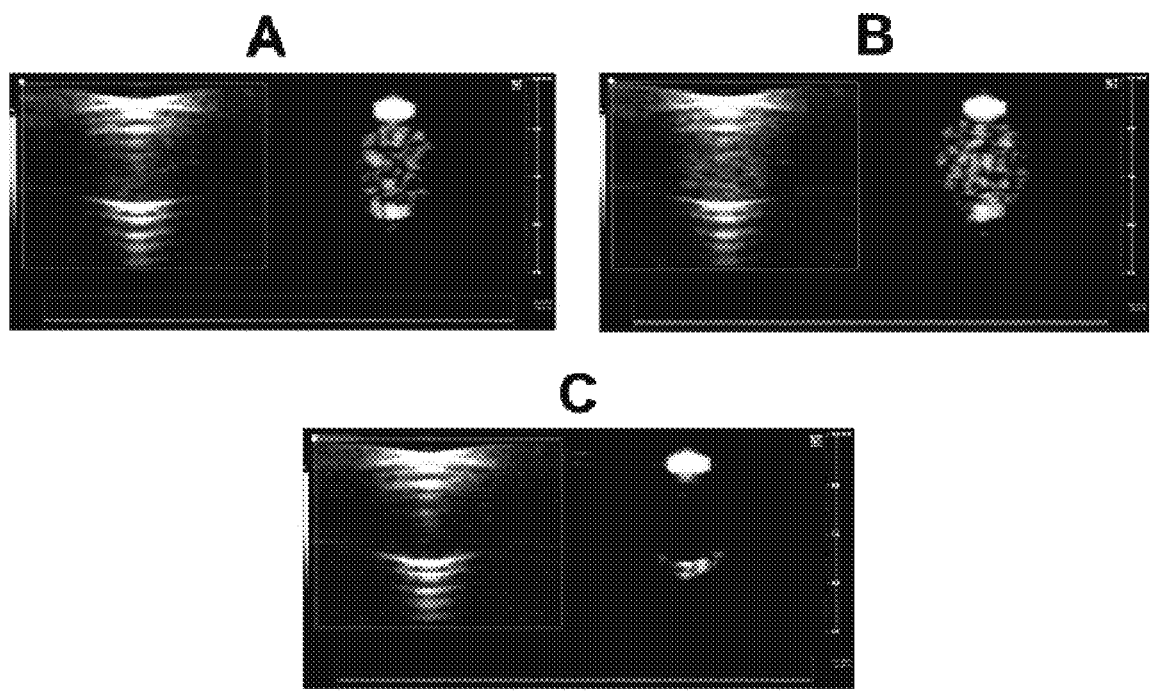
FIGS. 9A-C are images from a third experiment.
Figure 11:
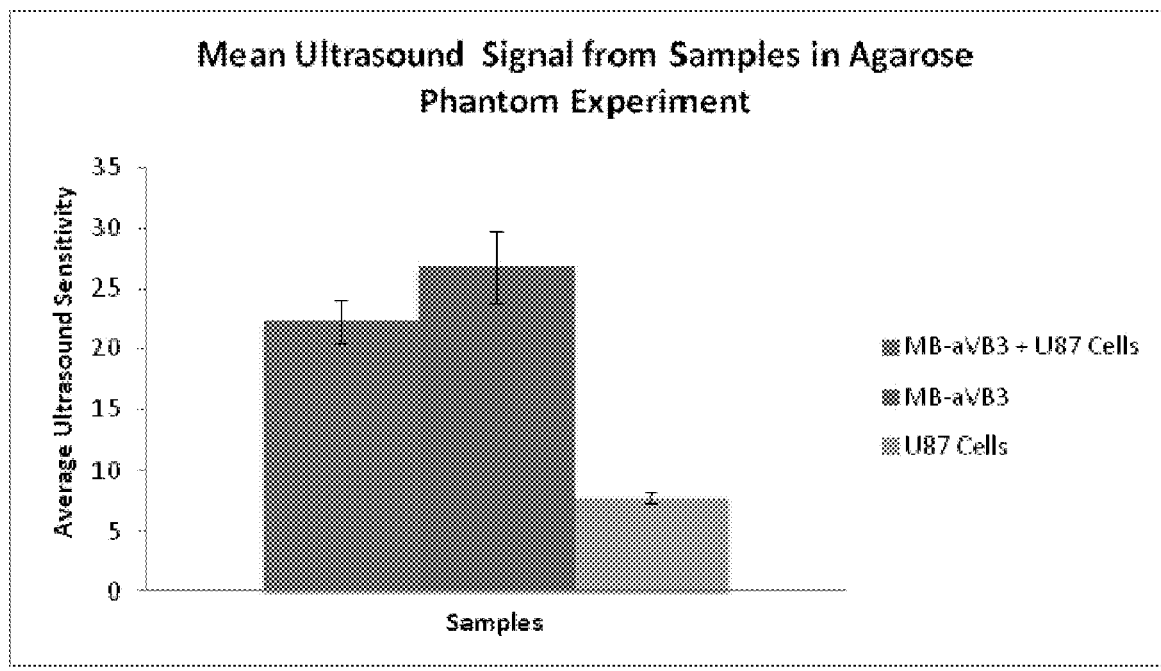
FIG. 11 is a graphical interpretation of the results from the third experiment.

In the third experiment, the three tests ($MB_{\alpha v \beta 3}$ bound to U87 cells, $MB_{\alpha v \beta 3}$ alone, and U87 cells alone) were analyzed using Image J to determine the average ultrasound signal from each sample. FIGS. 9A-C shows an ultrasound image of $MB_{\alpha v \beta 3}$ pre-bound to U87 cells in 9A (B-scan shown in gray on the left, contrast mode image shown on the right), an ultrasound image of $MB_{\alpha v \beta 3}$ alone in 9B, and an ultrasound image of U87 cells alone in 9C. The $MB_{\alpha v \beta 3}$ bound to U87 cells (FIG. 9A) had an average signal of 22.29±1.78 relative units, $MB_{\alpha v \beta 3}$ alone (FIG. 9B) had an average signal of 26.79±2.95 relative units, and U87 cells alone (FIG. 9C) had an average signal of 7.70±0.46 relative units. These results illustrate that the ultrasound signal from $MB_{\alpha v \beta 3}$ with U87 cells was higher than the ultrasound signal from U87 cells alone, as proof of concept for the ability to detect $MB_{\alpha v \beta 3}$ bound to CTCs in a blood vessel. Graphical interpretation of the results is displayed below under the graph of FIG. 11.

Discussion

In order to prove the concept for an embodiment of this invention, three main experiments were performed. The first experiment involved combining MBs with highly fluorescent FITC molecules so that the microbubbles could easily be distinguished from other materials under a fluorescent microscope. After post-experiment image analysis, it was determined that the fluorescent signal from $MB_{FITC}$ was much higher than the signal from just $MB_{PBS}$. At the same contrast ranges, the signal from $MB_{PBS}$ was close to 0, compared to a higher signal from $MB_{FITC}$. U87 cells were then combined with $MB_{FITC}$ and the two were easily distinguishable under the fluorescent microscope. As a control, $MB_{PBS}$ were added to a well of cells. When the combination of U87 cells and $MB_{FITC}$ was observed under the fluorescent microscope, it was found that the bright field setting could easily see the cells, but not the MBs, and that the fluorescent settings could easily see the MBs, but not the cells. However, some dead cells did fluoresce. This was probably due to endocytosis of MBs that happens as a cell dies and additional, natural fluorescence signal that is released during the time of cell death. This experiment proved that MBs and cells could easily be distinguished with the help of FITC molecules and fluorescence imaging.

For the second experiment, $MB_{\alpha v \beta 3}$ were created, and their effectiveness compared to $MB_{isotype}$ and the blocking study. Instead of targeting EpCAM receptors that are present on many CTCs, Alpha V Beta 3 Integrin ($\alpha v \beta 3$) was targeted, which is a receptor present on the surface of U87 cells. The characteristics and targeting methods are similar for both receptors, so successful attachment of targeted MBs to one receptor would prove successful attachment of targeted MBs to another receptor. After running the samples through a flow chamber and imaging them with a fluorescent microscope, we could see that the $MB_{\alpha v \beta 3}$ were clearly bound to many receptors on the surface of cells, while the $MB_{isotype}$ and the blocking study had less successful binding to cells. This experiment proved that the $MB_{\alpha v \beta 3}$ were successful in their binding to the $\alpha v \beta 3$ receptors, due to the difference in the MBs/field compared to the controls.

In the final experiment, $MB_{\alpha v \beta 3}$ bound to U87 cells were synthesized, and their ultrasound signal was compared to $MB_{\alpha v \beta 3}$ alone and U87 cells alone. An agarose phantom was constructed and connected to a syringe pump to simulate the conditions of a blood vessel in a controlled setting. After running the samples through the agarose phantom and analyzing the images, it was found that the signal from the $MB_{\alpha v \beta 3}$ bound to U87 cells and the $MB_{\alpha v \beta 3}$ alone was higher than the signal from U87 cells alone. This experiment helps prove that the ultrasounds signal from $MB_{\alpha v \beta 3}$ bound to CTCs in a blood vessel would be differentiable from ultrasound signal from a blood vessel without microbubbles.

CONCLUSIONS

Microbubbles conjugated with biotinylated human anti-$\alpha v \beta 3$ antibodies can attach onto receptors on U87 cells and be visualized in-vitro using ultrasound technology. These results are proof of concept for the detection of circulating tumor cells using microbubbles targeted for EpCAM.

These experiments have demonstrated the ability to use microbubbles conjugated with antibodies as a means of detecting cancer cells via ultrasound. In addition, the experiments illustrate that the ultrasound signal from U87 cells and cell media alone produce minimal ultrasound signal compared to the signal from $MB_{\alpha v \beta 3}$. These are the first key steps in developing a wearable autonomous real-time sensor for monitoring the presence of circulating tumor cells.

An embodiment of the invention provides a wearable ultrasound imaging device for detecting circulating tumor cells (CTC) in a cancer patient in vivo, in real time, by monitoring blood flow through a vein on the wrist, or some other easily assessable point. The device would primarily be used by a trained professional in a clinical setting to ensure no adverse reaction by the patient to the imaging agents. The clinician would help the patient put on the device, load it with a contrast agent, and initiate the device. The device would administer a controlled amount of contrast agent into the patient, potentially through an existing Chemo-port, then the detection system would begin to monitor for imaging agents bound to CTCs. The imaging agent would be designed to bind with unique receptors on circulating tumor cells, such as EpCAM, to ensure that only CTCs are measured. The real-time data collected by the detection device would be transmitted to a small computing device, such as a smart phone, for signal processing, analysis and display for clinical interpretation of results.

In different embodiments, the mechanism for administering the microbubbles can range from a manual injection by a clinician, to an automated injection by the device using a syringe pump. The microbubble injection could be through needle injection, or into an existing catheter or Chemo-port. In the automated case using a syringe pump, the device would not synthesize the microbubbles. The device would be a repository for holding the microbubbles and then injecting them into the patient. Following administering the microbubbles the detection device needs to be activated. This could be done manually by the clinician, or in the automated case, through communication between the injection device and the detection device, or most likely done through a smart phone application providing system level coordination.

In different embodiments, microbubbles could be loaded into a reservoir connected to the patient's chemo port periodically injecting the microbubbles (This could be done by communication between the ultrasonic wristband device and the reservoir); Microbubble components could be ingested orally, absorbed, and formed in the bloodstream (pills similar to these are being developed); or a nurse or patient could manually administer the microbubbles intravenously.

In an embodiment, the wearable ultrasound device will be used to detect the CTCs. It will not store the data, analyze the number of CTCs per mL of blood, or provide any clinical interpretation of the results. The molecular image data will be transmitting to a separate computing device, such as a smart phone application for data collection, data storage, analysis, interpretation of results, and display of results for the clinician.

Similar to other wearable diagnostic devices, the information the device collects would be immediately synchronized to a smart phone or other electronic device either via Bluetooth or Wi-Fi. This could be developed on a wearable device platform (Google, Apple, and others are currently working on such a platform) to standardize and simplify the application design and minimize or eliminate any hardware development required for the data communication, storage, analysis and display.

In other embodiments, the device could use different ultrasound contrast agents which would be used and detected in a similar manner as the microbubbles. In other embodiments, the device could implement different imaging modalities such as optical coherence tomography, fluorescence imaging, nuclear magnetic resonance, etc. . . . In other embodiments, different contrast agents such as gold nanorods, fluorescent proteins, and magnetic nanoparticles could be used with the appropriate imaging modality. In other embodiments, the device could detect other types of cells that express uncommon antibodies or proteins on their surfaces (such as lymphoma cells). Such uncommon cells in the blood stream are trace cells. As more and more surface proteins and receptors on CTCs are discovered, the targeted microbubbles could be coated with additional antibodies/proteins that attach to any new target. In other embodiments, the targeted microbubbles could be comprised of several antibodies/proteins targeted for various surface markers on CTCs. In different embodiments, the device could either implement 1D A-scans or A-scans in addition to B-scans to create 2D ultrasound images. In some embodiments, the device could use an algorithm in order to detect the location of a blood vessel and the presence of microbubbles using either a 1D or 2D ultrasound image to improve robustness of the detection and compensate for potential movement of the device relative to the blood vessel.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A system for detecting circulating tumor cells in a patient, comprising:
   microbubbles with an outer coating of antibodies, which attach to circulating tumor cells;
   an imaging agent injector for injecting the microbubbles into the patient, wherein circulating tumor cells are attached to the microbubbles;
   a support system for mounting on the patient;
   an ultrasonic imaging system attached to the support system, comprising;
   an ultrasonic transmitter and receiver system for generating and transmitting ultrasonic signals into the patient and receiving ultrasonic signals from the patient; and
   a controller, comprising:
   a processor; and
   non-transient computer readable media, comprising:
      computer readable code for transmitting ultrasonic signals into the patient;
      computer readable code for receiving ultrasonic signals from the patent;
      computer readable code for determining the presence of in vivo circulating tumor cells from the received ultrasonic signals from the patient; and
      computer readable code for determining the number of circulating tumor cells in a location of detection of the patient.

2. The system, as recited in claim 1, wherein the ultrasonic transmitter and receiver system comprises:
   an ultrasonic transmitter attached to the support system; and
   an ultrasonic receiver attached to the support system, wherein the support system is wearable.

3. The system, as recited in claim 1, wherein the ultrasonic transmitter and receiver system is an integrated wearable unit that uses an ultrasonic transceiver to both transmit and receive.

4. The system, as recited in claim 3, wherein the ultrasonic imaging system further comprises a remote computer system, comprising:
   a processor in the remote computer system, comprising; and
   non-transient computer readable media, comprising:
      computer readable code for receiving data from the processor of the controller;
      computer readable code for determining a location of blood vessels in a patient;
      computer readable code for providing Doppler analysis data from the received data; and
      computer readable code for determining circulating tumor cell flow per volume flow of blood.

5. The system, as recited in claim 4, wherein the remote computer system, further comprises computer readable code for creating an image from the Doppler analysis data and the circulating tumor cell imaging agent data.

6. The system, as recited in claim 5, wherein the remote computer system is a wireless communications device.

7. The system, as recited in claim 1, wherein the non-transient computer readable media further comprises computer readable code for providing blood flow data from the received signals from the patient.

8. The system, as recited in claim 7, wherein the blood flow data comprises volume of blood flow within a blood vessel data.

9. The system, as recited in claim 1, wherein the ultrasonic imaging system further comprises a remote computer system, comprising:
- computer readable code for receiving data from the processor;
- computer readable code for determining a location of blood vessels in a patient;
- computer readable code for providing Doppler analysis data from the received data; and
- computer readable code for determining circulating tumor cell flow per volume flow of blood.

10. The system, as recited in claim 1, wherein the imaging agent injector, comprises:
- a microbubble reservoir containing the microbubbles;
- an injector in fluid communication with the microbubble reservoir;
- a motor for moving microbubbles from the microbubble reservoir to the injector;
- an injector controller for controlling the motor; and
- at least one battery adapted to power the injector, the motor, and the injector controller, wherein the imaging agent injector is wearable.

11. The system, as recited in claim 1, wherein the computer readable code for determining the number of circulating tumor cells in a location of detection of the patient determines the number of circulating tumor cells in a plurality of blood vessels at the location of detection.

12. The system, as recited in claim 1, wherein the computer readable code for determining the presence of in vivo circulating tumor cells from the received ultrasonic signals from the patient determines the presence of in vivo circulating tumor cells after microbubbles not bound to circulating tumor cells are flushed out of the patient.

* * * * *